US012167883B2

(12) United States Patent
Huffer et al.

(10) Patent No.: US 12,167,883 B2
(45) Date of Patent: Dec. 17, 2024

(54) MEDICAL DEVICE INCLUDING EXPANDABLE MUSCLE POLYMER

(71) Applicant: BARD PERIPHERAL VASCULAR, INC., Franklin Lakes, NJ (US)

(72) Inventors: Katherine Huffer, Chandler, AZ (US); Brandon Simmons, Tempe, AZ (US); Mark Nicholas Wright, Gilbert, AZ (US); Ronda Allard, San Tan Valley, AZ (US); Casey Hebert, Loveland, CO (US)

(73) Assignee: BARD PERIPHERAL VASCULAR, INC., Franklin Lakes, NJ (US)

( * ) Notice: Subject to any disclaimer, the term of this patent is extended or adjusted under 35 U.S.C. 154(b) by 0 days.

(21) Appl. No.: 18/022,621

(22) PCT Filed: Sep. 11, 2020

(86) PCT No.: PCT/US2020/050301
§ 371 (c)(1),
(2) Date: Feb. 22, 2023

(87) PCT Pub. No.: WO2022/055491
PCT Pub. Date: Mar. 17, 2022

(65) Prior Publication Data
US 2023/0240739 A1 Aug. 3, 2023

(51) Int. Cl.
*A61B 18/18* (2006.01)
*A61B 18/08* (2006.01)
*A61B 18/00* (2006.01)

(52) U.S. Cl.
CPC .. *A61B 18/082* (2013.01); *A61B 2018/00136* (2013.01); *A61B 2018/00154* (2013.01);
(Continued)

(58) Field of Classification Search
CPC ...... A61B 18/1492; A61B 2018/00577; A61B 2018/0022; A61B 2018/00214;
(Continued)

(56) References Cited

U.S. PATENT DOCUMENTS 5,545,210 A * 8/1996 Hess ..................... A61F 2/86
606/198
9,387,305 B2 * 7/2016 Courtney ............ A61M 39/223
(Continued)

FOREIGN PATENT DOCUMENTS

WO 0056237 A2 9/2000
WO 2008008427 A2 1/2008
(Continued)

OTHER PUBLICATIONS

Kaplon Tomasz et al: "Induction heating for a silicone/ethanol composite actuator", 2020 International Conference Methatronic Systems and Materials (MSM), IEEE, Jul. 1, 2020.

*Primary Examiner* — Michael F Peffley
*Assistant Examiner* — Amanda L Zink
(74) *Attorney, Agent, or Firm* — Dickinson Wright PLLC; Andrew D. Dorisio (57) ABSTRACT

A medical device for treating coronary artery disease, peripheral arterial disease or varicose veins includes an elongated support and a heat expandable element of muscle polymer carried on that elongated support. The medical device may also include a heating element. When activated, the heating element produces heat that causes the muscle polymer to expand into a position in closer proximity to the tissue to be treated.

34 Claims, 8 Drawing Sheets

(52) U.S. Cl.
CPC ............... *A61B 2018/0022* (2013.01); *A61B 2018/00404* (2013.01); *A61B 2018/0041* (2013.01); *A61B 2018/00422* (2013.01); *A61B 2018/00577* (2013.01); *A61B 2018/00601* (2013.01)

(58) Field of Classification Search
CPC .... A61B 17/12136; A61B 2018/00285; A61B 2018/0016; A61B 2018/00351
See application file for complete search history.

(56) References Cited

U.S. PATENT DOCUMENTS

| | | | |
|---|---|---|---|
| 10,973,561 B2* | 4/2021 | Caplan | A61B 18/04 |
| 11,419,659 B2* | 8/2022 | Levin | A61B 18/04 |
| 11,565,078 B2* | 1/2023 | Rajagopalan | A61B 5/4836 |
| 11,703,257 B2* | 7/2023 | Liu | F03G 7/06 |
| | | | 57/250 |
| 2007/0191919 A1* | 8/2007 | Lui | A61N 1/057 |
| | | | 607/116 |
| 2008/0033524 A1* | 2/2008 | Gale | A61F 2/958 |
| | | | 606/108 |
| 2014/0276718 A1 | 9/2014 | Turovskiy | |
| 2020/0138505 A1* | 5/2020 | Levin | A61B 18/04 |
| 2020/0297408 A1* | 9/2020 | Mori | A61B 18/1477 |

FOREIGN PATENT DOCUMENTS

| | | |
|---|---|---|
| WO | 2008086613 A1 | 7/2008 |
| WO | 2014150595 A1 | 9/2014 |
| WO | 2019018362 A1 | 1/2019 |
| WO | 2019116629 A1 | 6/2019 |
| WO | 2020159865 A1 | 8/2020 |

* cited by examiner

MEDICAL DEVICE INCLUDING EXPANDABLE MUSCLE POLYMER

TECHNICAL FIELD

This disclosure relates generally to medical devices and, more particularly, to a medical device including an elongated support and a heat expandable element made from a muscle polymer.

BACKGROUND

Varicose veins are veins that have become enlarged and twisted. Varicose veins are commonly found on the leg but may occur at other locations. Varicose veins may bulge and usually have a blue and/or purple color causing them to be a cosmetic concern for many afflicted by the condition.

For some, varicose veins are associated with disconcerting symptoms, including but not necessarily limited to, burning, throbbing, itching and a heavy feeling in the afflicted legs.

Varicose veins are generally associated with a compromised ability to properly carry blood flow back to the heart and blood may accumulate in the veins causing the bulging. More particularly, varicose veins contain leaky valves which cause the blood to flow backward towards the lower limbs and feet. Phlebitis or inflammation of the inside lining of the afflicted vein may occur and blood clots may form.

SUMMARY

This disclosure relates to a new and improved medical device incorporating an elongated support and a heat expandable element made from a muscle polymer. The medical device is useful for a number of different applications including, but not necessarily limited to, percutaneous transluminal angioplasty (PTA) and for ablating tissue associated with varicose veins.

This disclosure also relates to a new method of customizing the medical device to the vasculature of a specific patient undergoing treatment. Such a customized medical device allows for more efficient and effective medical treatment.

In accordance with the purposes and benefits described herein, a new and improved medical device is provided. According to one aspect of the disclosure, there is provided a medical device comprising: an elongated support and a heat expandable element carried on the elongated support. In one or more embodiments, the medical device further includes a heating element associated with the heat expandable element. When the heating element is activated, the heat expandable element expands to displace the heat expandable element from a contracted position to an expanded position in closer proximity to the tissue to be ablated. For purposes of this document, the terminology "closer proximity" includes direct contact with the tissue to be ablated.

The heat expandable element may be a body made from a muscle polymer. For purposes of this document, "muscle polymer" refers to an elastomeric polymer including embedded micro-bubbles of liquid-gas phase change material having a phase change temperature between 40-100° C. In one or more embodiments, the muscle polymer has a phase change temperature of between 40-60° C.

The elastomeric polymer of the muscle polymer may be selected from a group of elastomeric polymers consisting of silicone, thermoplastic elastomer, styrenic (TPE-S) and combinations thereof. The liquid-gas phase change material of the muscle polymer may be selected from a group of liquid-gas phase change materials consisting of ethanol, butanol and combinations thereof.

In one or more of the many possible embodiments of the medical device, the muscle polymer is silicone-ethanol.

In one or more of the many possible embodiments of the medical device, the body may be a sleeve 3-D printed onto the elongated support. In one or more of the many possible embodiments of the medical device, the body may be molded onto the elongated support. In one or more of the many possible embodiments of the medical device, the body extends 360° around the elongated support.

In one or more of the many possible embodiments of the medical device, the elongated support is a lumenless shaft. In one or more of the many possible embodiments of the medical device, the elongated support is a catheter. That catheter may include one or more lumens. Such lumens may function (a) to receive a guide wire, (b) to allow drug delivery to plaques or tissues to be treated or (c) for any other useful purpose.

In one or more of the many possible embodiments of the medical device, the elongated support includes a proximal end and a distal end. In one or more of the many possible embodiments of the medical device, the proximal end includes a handle.

In one or more of the many possible embodiments of the medical device, the handle includes an actuator to control operation of the heating element. The actuator may be selected from a group consisting of a push button, a toggle switch, a slide switch and a twist knob.

In one or more of the many possible embodiments of the medical device, the handle houses a power source adapted to power the heating element. In one or more of the many possible embodiments of the medical device, the handle includes a power cord configured for connection to a remote power supply. In one or more of the many possible embodiments of the medical device, the handle includes a drug delivery port.

In one or more of the many possible embodiments of the medical device, the heating element is a resistive wire at least partially embedded in the heat expandable element. In one or more of the many possible embodiments of the medical device, the resistive wire extends from the handle through the elongated support to the heat expandable element. In one or more of the many possible embodiments of the medical device, the resistive wire includes an array of resistive wires extending around a circumference of the elongated support in the heat expandable element.

In one or more of the many possible embodiments of the medical device, a wire connecting cap is provided at the distal end of the elongated support.

In one or more of the many possible embodiments of the medical device, the medical device further includes a scoring element carried on the muscle polymer. That scoring element may comprise at least one wire.

In one or more of the many possible embodiments of the medical device, the muscle polymer has a corrugated profile: that is, includes alternating furrows and ridges. The corrugated profile may be in a transverse direction or in a longitudinal direction.

In one or more of the many possible embodiments of the medical device, the muscle polymer includes at least one flow channel extending from a first longitudinal end of the muscle polymer to a second longitudinal end of the muscle polymer. When expanded in a vein, such a flow channel allows blood to flow past the expanded muscle polymer.

In one or more of the many possible embodiments of the medical device, the medical device further includes an insulating membrane over an outer surface of the muscle polymer. That insulating membrane may comprise, for example, a silicone polymer coating.

In accordance with an additional aspect, a new and improved method is provided for ablating tissue in a vein of a patient. That method comprises the steps of: (a) positioning an elongated support in the vein, (b) activating a heating element associated with a heat expandable element carried on the elongated support and (c) expanding the heat expandable element in response to heat from the heating element and thereby displacing the heating element into closer proximity to the tissue to be ablated.

In one or more of the many possible embodiments of the method, the method includes the steps of (a) deactivating the heating element and (b) contracting the heat expandable element in response to cooling of the heating element.

In one or more of the many possible embodiments of the method, the method includes the step of repositioning the elongated support in the vein.

In one or more of the many possible embodiments of the method, the method includes the steps of (a) reactivating the heating element and (b) re-expanding the heat expandable element in response to the heat from the reactivated heating element and thereby displacing the heating element into closer proximity to additional tissue to be ablated.

In one or more of the many possible embodiments of the method, the method includes the step of using a body made from a muscle polymer as the heat expanding element.

In one or more of the many possible embodiments of the method, activating the heating element includes directing a current through a resistive wire embedded in the heat expandable element.

In one or more of the many possible embodiments of the method, the method includes the step of expanding the heat expandable element to an expanded position by heating micro-bubbles of a liquid-gas phase change material embedded in an elastomeric polymer of the heat expandable element to a temperature sufficient to cause a phase change from liquid to gas.

In one or more of the many possible embodiments of the method, the method includes the step of contracting the heat expandable element to a contracted position by cooling micro-bubbles of a liquid-gas phase change material embedded in an elastomeric polymer of the heat expandable element to a temperature sufficient to cause a phase change from gas to liquid.

In the following description, there are shown and described several embodiments of the medical device and related method for ablating tissue including, particularly problematic tissue associated with varicose veins and for removing plaques and lesions associated with coronary heart disease. As it should be realized, the medical device and method are capable of other, different embodiments and their several details are capable of modification in various aspects all without departing from the medical device and method as set forth and described in the claims. Accordingly, the drawings and descriptions should be regarded as illustrative rather than restrictive.

BRIEF DESCRIPTION OF THE DRAWING FIGURES

The accompanying drawing figures incorporated herein and forming a part of this patent specification, illustrate several aspects of the medical device and related method and together with the description serve to explain certain principles thereof.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed medical devices and methods may be practiced without these specific details. In other instances, well-known methods, procedures, components, or structures may not have been described in detail so as not to obscure other details of the novel medical device and method.

The description provided below and in regard to the figures applies to all embodiments unless noted otherwise, and features common to each embodiment are similarly shown and numbered.

Reference is now made to FIGS. 1-4 illustrating one possible embodiment of the new and improved medical device 10 adapted for treating plaques and lesions associated with coronary heart disease and ablating problematic tissue associated with varicose veins. The medical device 10 generally includes (a) an elongated support 12, (b) a heat expandable element 14 carried on the elongated support and (c) a heating element 16 associated with the heat expandable element. When the heating element 16 is activated, the heat expandable element 14 expands from a rest or contracted position to an expanded position in closer proximity to the tissue to be ablated.

Figure 7:
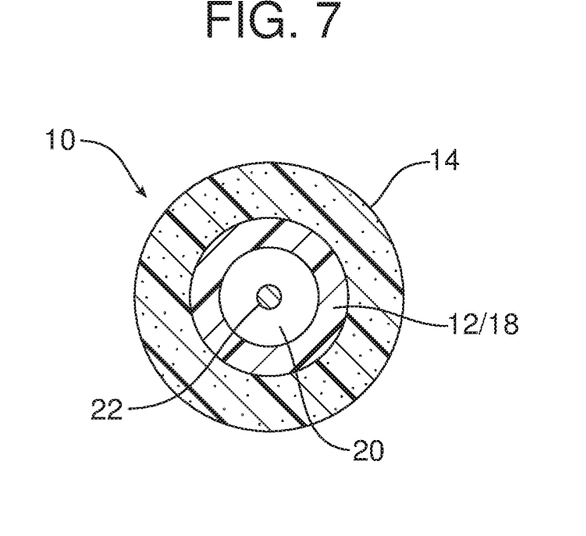
FIG. 7 is a transverse cross-sectional view of an alternative embodiment of the medical device wherein the elongated support is a catheter instead of the lumenless shaft illustrated in the embodiment of FIGS. 1-6B.

In the embodiment of FIGS. 1-4, the elongated support 12 takes the form of a lumenless shaft. In an alternative embodiment shown in FIG. 7, the elongated support 12 takes the form of a catheter including a tubular wall 18 surrounding a lumen 20. The lumen 20 may be adapted to receive a guidewire 22 to aid in placement of the elongated support/catheter in a varicose vein. While only one lumen 20 is shown in FIG. 7, multiple lumens may be provided if desired.

In any of the illustrated embodiments, the elongated support 12 may be made from any appropriate material including but not necessarily limited to extruded polymer materials such as PEBAX® brand polyether block amide (PEBA), Nylon, polyethylene terephthalate (PET), etc. which may or may not be braided or loaded with radioopaque materials. The elongated support may also be a stainless steel or nitinol hypotube with or without cuts to increase flexibility which may or may not be laminated with various types of plastic (PEBAX® brand PEBA, Nylon, PET, etc.). The elongated support may have a circular cross section having a diameter of between about 3-16 French and a length of between about 35-250 cm suitable to allow for ablation of tissue during the PTA or varicose vein treatment.

In the embodiment illustrated in FIG. 1-4, the heat expandable element 14 takes the form of a body made from a muscle polymer. As best illustrated in FIGS. 5A and 5B, a muscle polymer comprises an elastomeric polymer material 23 including embedded micro-bubbles of liquid-gas phase change material 24 having a phase change temperature between 40-100° C. In some embodiments, the phase change temperature is between 40-60° C.

As will be explained in greater detail below, when the heat expandable element or body 14 is maintained at a temperature below the phase change temperature of the phase change material 24, the phase change material is in a liquid state and the heat expandable body is maintained in a rest or contracted state or position (See FIG. 5A). In contrast, when the heat expandable element or body 14 is heated to a temperature above the phase change temperature, the phase change material phases to a gas state, increasing in volume and thereby expanding the heat expandable element or body (See FIG. 5B and compare to FIG. 5A).

The elastomeric polymer of the heat expandable element or body 14 may be selected from a group of elastomeric polymer materials including, but not necessarily limited to silicone, TPE-S and combinations thereof.

The liquid-gas phase change material of the heat expandable element or body 14 may be selected from a group of liquid-gas phase change materials including, but not necessarily limited to ethanol, butanol and combinations thereof.

One particularly useful muscle polymer is silicone-ethanol. Such a material has a relatively high strain of up to 900%, a relatively high stress of up to 1.3 MPa and a relatively low density of about 0.84 g/cm$^3$.

The heat expandable element 14 may comprise a sleeve 3-D printed onto the elongated support 12. In other embodiments, the heat expandable element 14 may comprise a sleeve cast or molded onto the elongated support 12. In the illustrated embodiment, the heat expandable element or body 14 extends 360° around the elongated support 12. In other embodiments, the heat expandable body 14 may extend only partially around the support 12. In the illustrated embodiment, the heat expandable element or body 14 is of equal thickness around the circumference of the elongated support 12. In other embodiments, the thickness of the heat expandable element 14 may be varied around the circumference of the elongated support 12.

As further illustrated in FIG. 1-4, the elongated support includes a proximal end 26 and a distal end 28. As illustrated, the distal end 28 may include a rounded tip 27 to aid in inserting and displacing the medical device 10 into and through the vasculature of a patient. As illustrated, the proximal end 26 includes a handle 30. The handle 30 may be made from various types of plastic (e.g. acrylonitrile butadiene styrene (ABS), polyoxymethylene, polycarbonate, etc.) that may or may not be coated with a soft silicone grip. The handle 30 may be cylindrical in shape or contoured.

Figure 1:
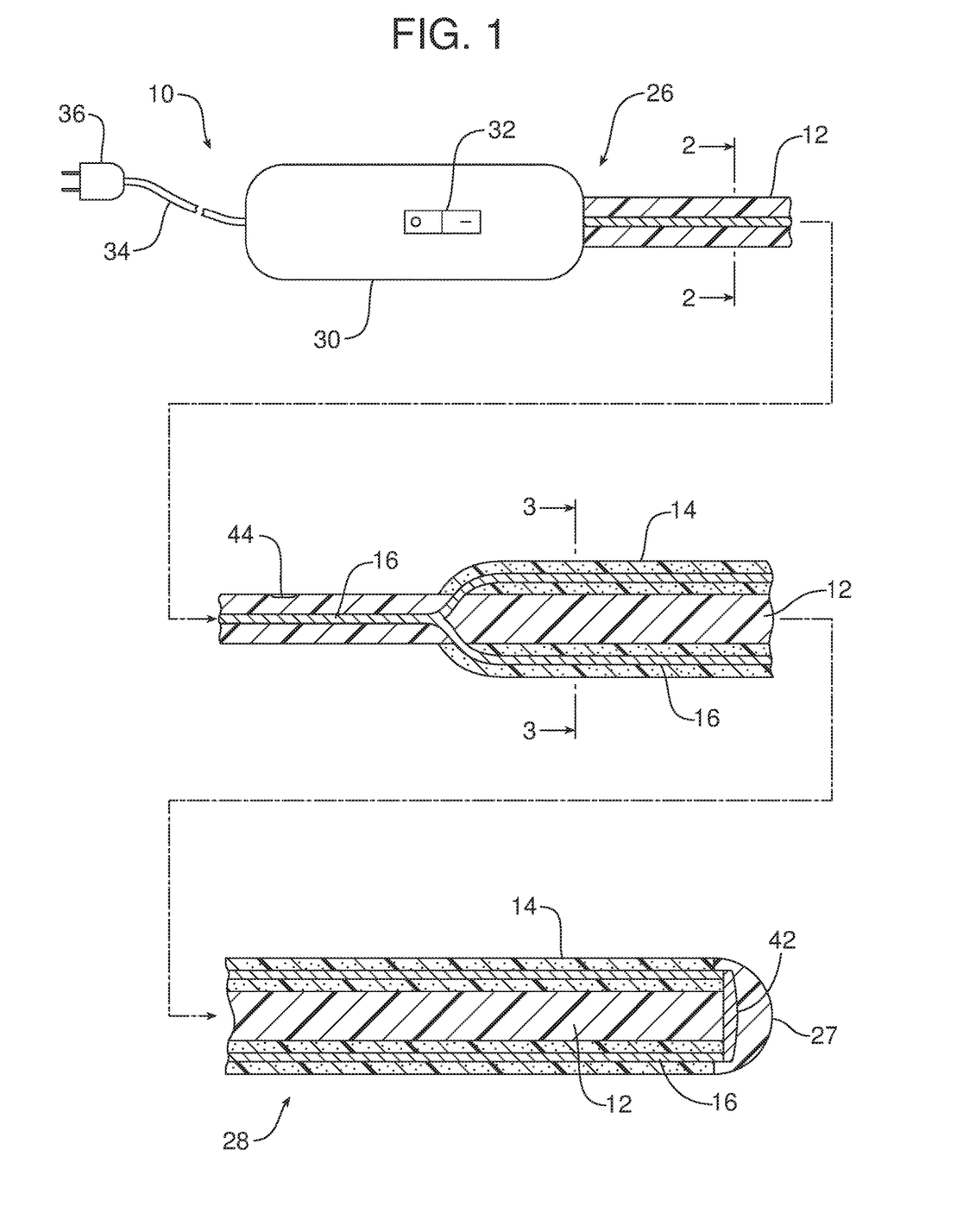
FIG. 1 is a longitudinal, partially cross-sectional view of the new and improved medical device for heat ablating tissue illustrating the heat expandable element or body in a first rest or contracted position.
Figure 2:
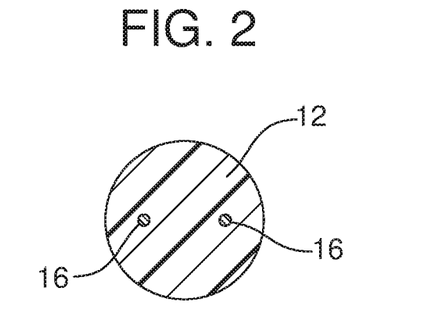
FIG. 2 is transverse cross-sectional view at line 2-2 of FIG. 1.
Figure 4:
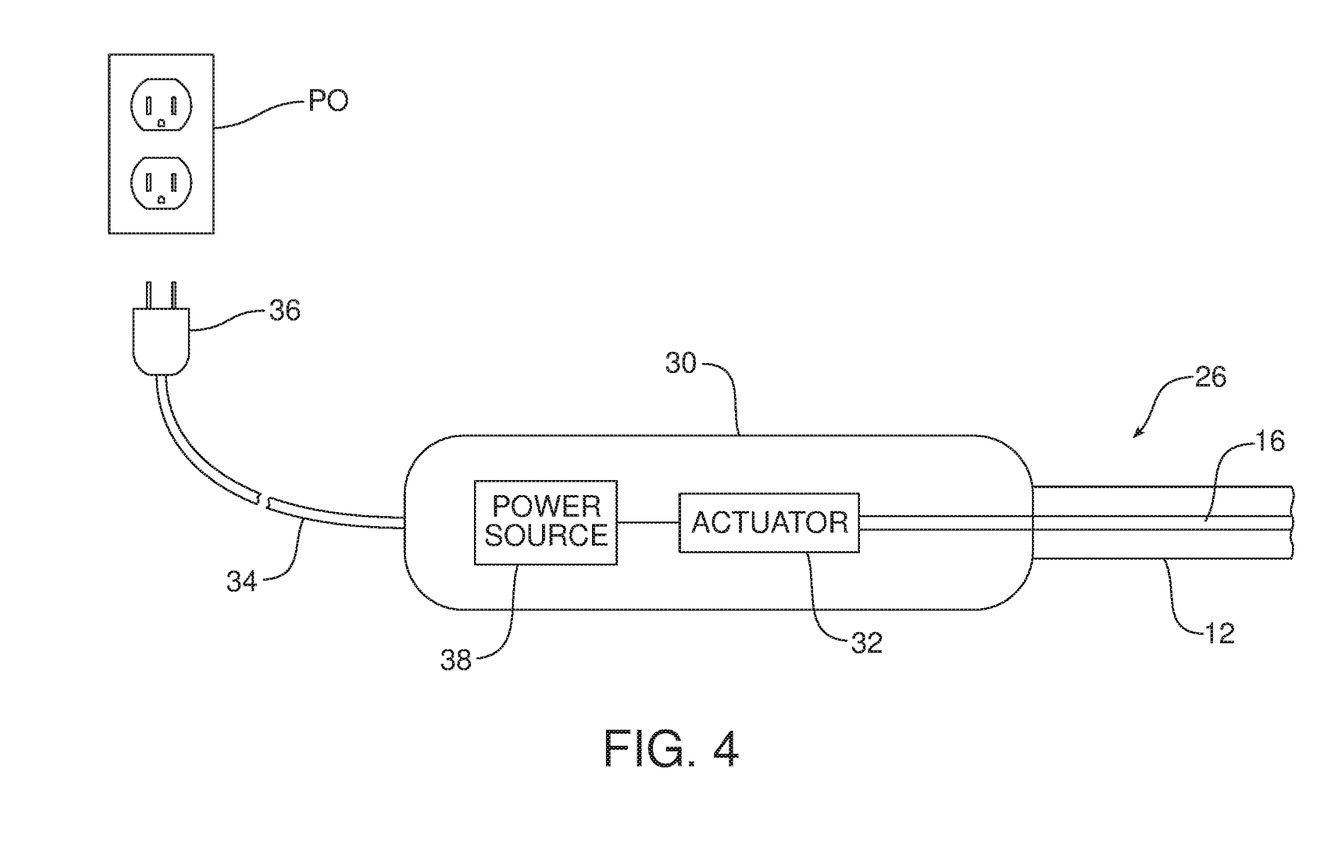
FIG. 4 is a detailed schematic illustration of one possible embodiment of the handle of the medical device provided on the proximal end of the elongated body.
Figure 5A:
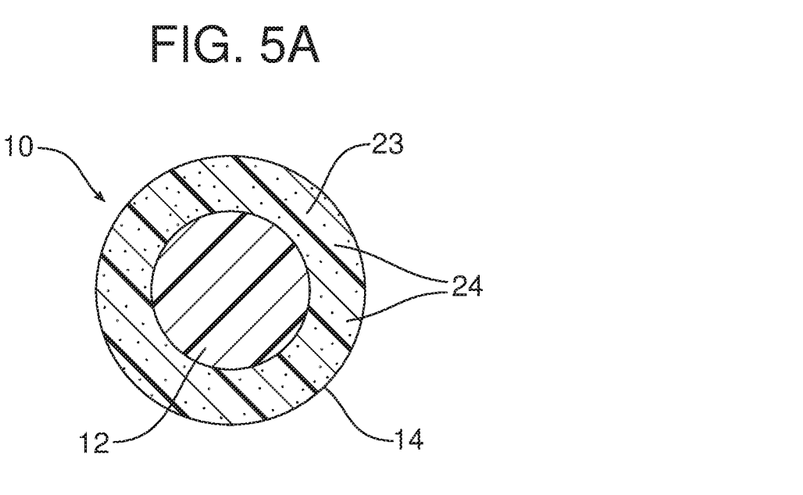
FIGS. 5A and 5B are respective detailed schematic illustrations of the body of muscle polymer in (a) the rest or contracted position and (b) the expanded position.
Figure 5B:
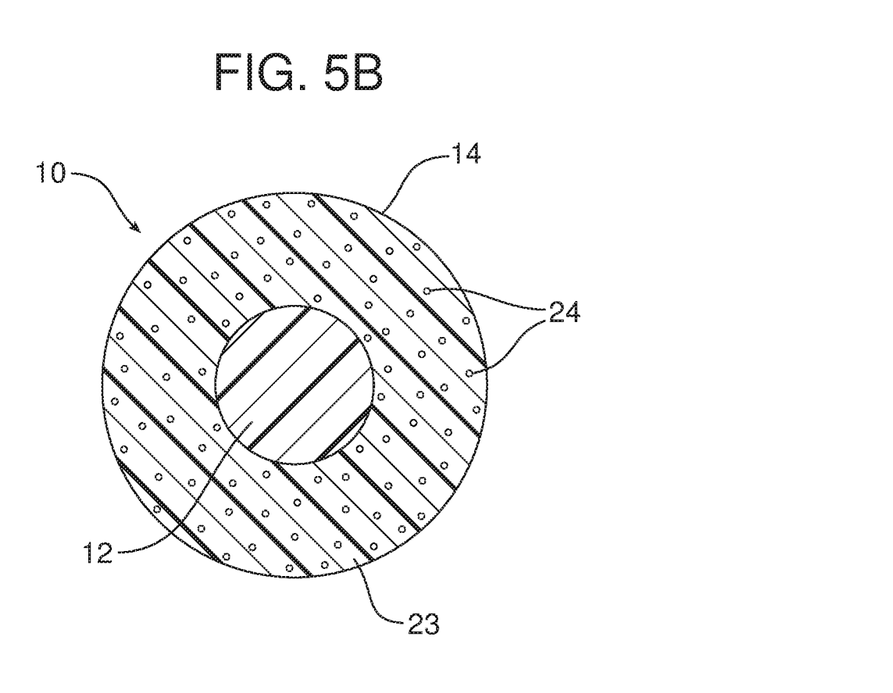

As illustrated in FIGS. 1 and 4, the handle may include an actuator 32 adapted to control the operation of the heating element 16. In the illustrated embodiment, the actuator 32 is a toggle switch having "on" and "off" positions. In other embodiments, the actuator 32 may take the form of a push button, a dial, a slide switch or a twist knob as is well known in the art.

As illustrated in FIGS. 1 and 4, the handle may include a power cord 34 having an electrical plug 36 on the end thereof, adapted for connection to a remote power source such as a standard electrical wall power outlet PO. In one or more of the many possible embodiments, the handle 30 may house a power source 38 adapted for powering the heating element 16. That power source 38 may comprise one or more batteries, one or more capacitors or the like. Some embodiments of the medical device 10 may include both the power cord 34 and the internal power source 38.

As also illustrated in FIGS. 1-4, the heating element 16 associated with the heat expandable element or body 14 comprises a resistive wire that extends from the actuator 32 in the handle 30, through the elongated support 12 to the heat expandable element or body 14. The heating element or resistive wire 16 may be embedded in the heat expandable element or body 14 where it is sealed from contact with the vasculature during a medical procedure.

Figure 3:
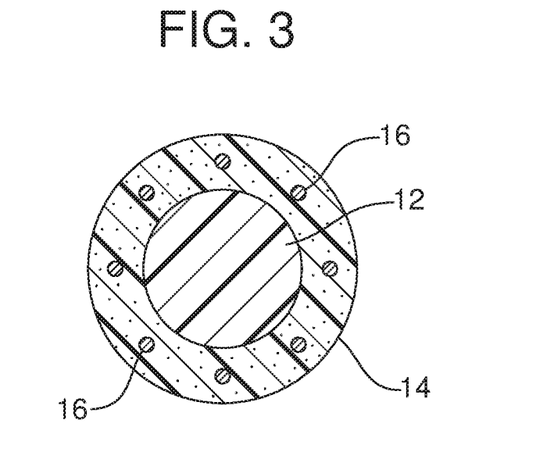
FIG. 3 is a transverse cross-sectional view at line 3-3 of FIG. 1.

As illustrated in FIG. 3, the resistive wire includes an array of resistive wires 16 extending around the circumference of the elongated support 12 and the heat expandable element 14. Of course, the shape and/or number of the heating elements 16 may vary. For example, the heating element 16 could be of helical shape coiled around the elongated support 12 within the heat expandable element or body 14. In other embodiments, the heating element 16 could be embedded in the elongated body 12, such as just under the outer surface thereof or on the outer surface thereof in intimate contact with the heat expandable element or body 14. The elongated body 12 could be skived to at least partially expose the heating element 16 to the overlying heat expandable element or body 14. A metal wire connecting cap 42 at the distal end 28 of the elongated support 12 completes the electrical circuit.

Figure 6A:
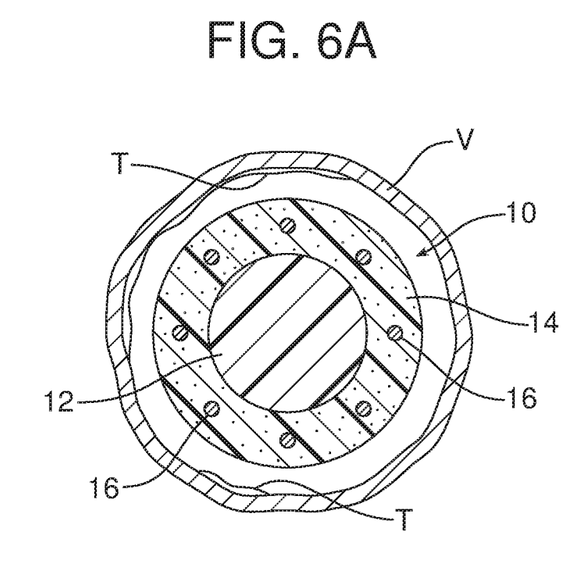
FIG. 6A is a transverse cross-sectional view illustrating the medical device of FIG. 1 in a varicose vein with the heat expandable element or body of muscle polymer in the rest or contracted position.

The medical device 10 is particularly suited for use in a method of ablating tissue including problematic tissue associated with coronary heart disease or varicose veins. That method includes the step of positioning the elongated support 12 in the vein V in the area of the tissue T to be ablated (see FIG. 6A). This is done while the heat expandable element 14 is in the rest or contracted position contracted tightly around the elongated support 12. Proper positioning of the elongated body 12 is possible through manipulation of the handle 30 in a manner known in the art. Echogenic markings 44 may be provided on the device 10, such as along the heat expandable element or body 14 to confirm positioning within the varicose vein.

Figure 6B:
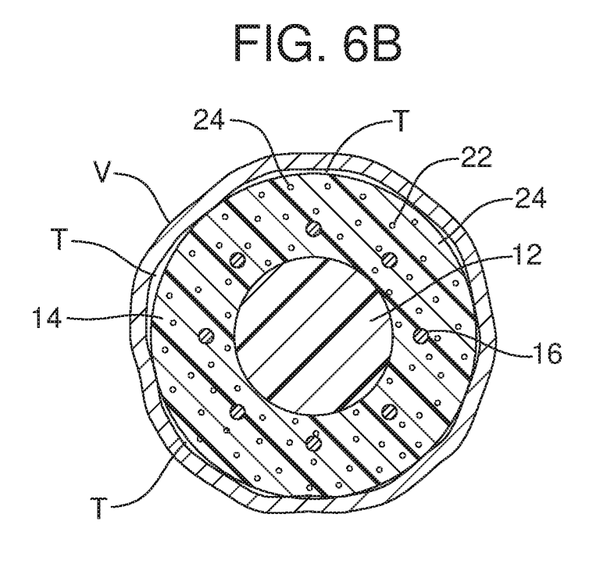
FIG. 6B is a view similar to FIG. 6A but illustrating the heat expandable element or body of muscle polymer in the expanded position in close proximity to the tissue to be ablated.

Once properly positioned in the varicose vein V, the method includes the step of activating the heating element 16 associated with the heat expandable element or body 14 carried on the elongated support 12. This is done by manipulation of the actuator 32 on the handle 30 and application of current through the resistive wire 16 embedded in the body. When the heating element 16 functions to heat the heat expandable element or body 14 above the phase change temperature of the micro-bubbles of liquid-gas phase change material 24 embedded in the body, the liquid phase change material phases to gas, expanding the heat expandable element or body from the contracted position illustrated in FIG. 6A to the expanded position illustrated in FIG. 6B. When expanded in this manner until stasis is achieved, the heat expandable element or body 14 is in close proximity, even touching the tissue T to be ablated. As the heat expandable element or body 14 continues to be heated by the heating element 16, the heat expandable element or body reaches a temperature necessary for ablation of the tissue T.

Advantageously, the absence of a lumen in the embodiment of the medical device 10 illustrated in FIGS. 1-6B allows the elongated support to be made with a smaller diameter which, in turn, allows the overall device to have a smaller diameter adapted to function in smaller veins including those veins in the lower extremities including below the knee.

Advantageously, the medical device 10 requires only one small incision for insertion of the elongated support 12 into the vasculature whereas traditional varicose vein procedures typically require a larger incision or multiple incisions. Thus, the medical device 10 and related method of ablating tissue T of a varicose vein V results in faster healing times.

Advantageously, the heat expandable element or body 14 made from the muscle polymer allows for uniform heating and ablation of tissue T over the entire length of the elongate support 12 that is covered with the heat expandable element or body. Thus, where a surgeon uses a medical device 10 with a longitudinal length of the heat expandable element or body 14 corresponding to the length of the area in the varicose vein requiring tissue ablation, the entire procedure can be completed with one placement of the device at one time.

Following tissue ablation, the actuator 32 is manipulated to deactivate the heating element 16. This, in turn, causes the heating element 16 and the heat expandable element or body 14 to cool. As the heat expandable element or body 14 cools to below the phase change temperature, the phase change material phases back to liquid. That liquid assumes a smaller volume of space than the gas, allowing the resilient memory of the elastomeric polymer material to shrink the heat expandable element or body back to its original size: that is, the body returns to its original rest or contracted position. The medical device 10 may then be easily removed from the vein V if the ablation procedure has been completed.

On the other hand, if further ablation of tissue T in another area of the vein V is required, the method may include the step of repositioning the elongated support 12 in the vein V adjacent the additional tissue to be ablated. This is then followed by the steps of (a) reactivating the heating element 16 by means of manipulation of the actuator 32 and (b) re-expanding the heat expandable element or body 14 in response to the heat generated by the heating element. As a result, the heat expandable element or body 14 and the heating element 16 contained therein is displaced outward from the elongated support closer to the tissue T to be ablated.

Following treatment of the additional tissue T at this new area, the medical device 10 may either be repositioned in the vein V again in order to treat tissue in another area or removed from the vein in the manner previously described.

Figure 8:
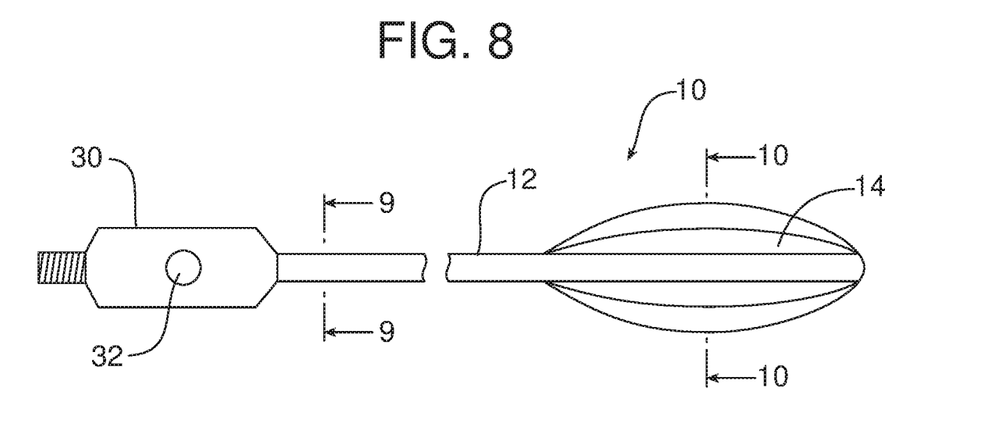
FIG. 8 is a side elevational view of an alternative embodiment of the medical device including a scoring element carried on the heat expandable element of muscle polymer.
Figure 9:
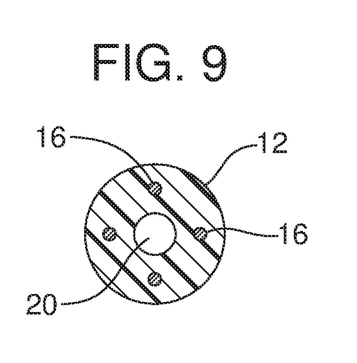
FIG. 9 is a transverse cross-sectional view taken along line 9-9 of FIG. 8.
Figure 10:
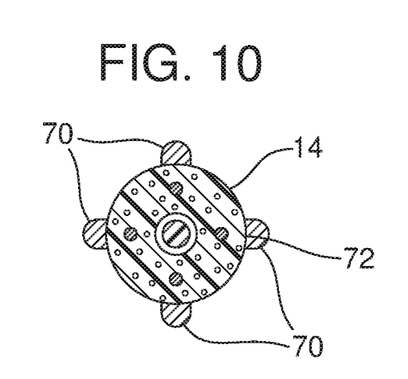
FIG. 10 is a transverse cross-sectional view taken along line 10-10 of FIG. 8.

Reference is now made to FIGS. 8-10 illustrating an alternative embodiment of the medical device 10 including: an elongated body 12 (in the form of a catheter having a lumen 20) having a heat expandable element 14 at a distal end and a handle 30 at a proximal end. A heating element 16 in the form of a plurality of resistive heating wires are embedded in the muscle polymer of the heat expandable element 14. A push button actuator 32 on the handle 30 allows for activation of the heating element 16 and heat expansion of the heat expandable element 14.

As illustrated in FIGS. 8 and 10, a scoring element 70 is carried on the muscle polymer of the heat expandable element. In the illustrated embodiment, the scoring element 70 comprises a plurality of wires carried upon and projecting from the outer surface 72 of the muscle polymer forming the heat expandable element 14. The wires may be made from metal or any other appropriate material for construction of a tissue scoring element.

Figure 11:
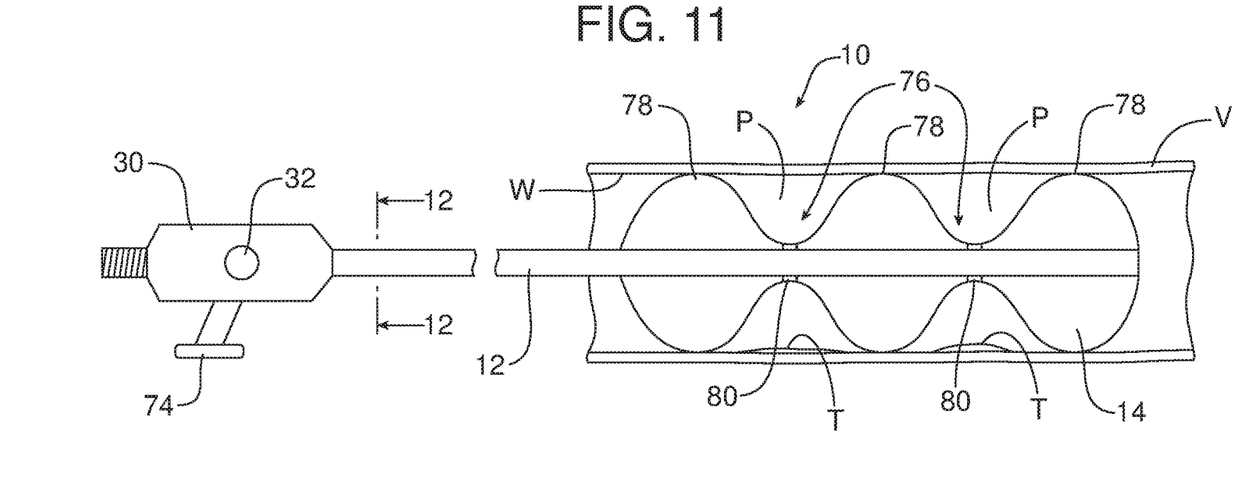
FIG. 11 is a side elevational view of yet another alternative embodiment of the medical device adapted for drug delivery to furrows formed in a heat expandable element of muscle polymer having a corrugated profile in the longitudinal direction.
Figure 12:
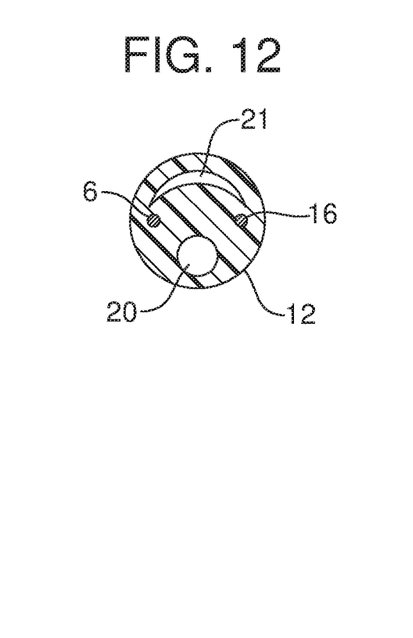
FIG. 12 is a transverse cross-sectional view taken along line 12-12 of FIG. 11.

Reference is now made to FIGS. 11 and 12 illustrating yet another possible embodiment of the medical device 10 including an elongated body 12 in the form of a catheter having a guidewire lumen 20 and a separate drug delivery lumen 21. A heat expandable element 14 of muscle polymer is provided at the distal end of the elongated body 12. A handle 30 is provided at the proximal end of the elongated body 12. The handle 30 carries a pushbutton actuator 32 for activating the heating element 16 and a drug delivery port 74 for injecting drugs through the drug delivery lumen 21 in a manner described below.

As illustrated in FIG. 11, when the heating element 16 is activated and the heat expandable element 14 is fully expanded, the heat expandable element has a corrugated profile in a longitudinal or length direction: that is, a plurality of alternating furrows 76 and ridges 78. In the illustrated embodiment, there are two furrows 76 and three ridges 78. It should be appreciated that other number of furrows and ridges may be provided.

As shown in FIG. 11, the ridges 78 seal against the wall W of the vein V and the two alternating furrows 76 form two annular pockets P with the wall W of the vein V. Drugs useful in dissolving plaques, removing lesions or ablating problematic tissue T may be injected into the drug delivery port 74 at the handle 30. Such drugs travel through the drug delivery lumen 21 along the length of the elongated body or catheter 12 to the drug delivery channels 80 that provide fluid communication between the drug delivery lumen 21 and the two pockets P.

As the pockets P fill with drugs, the drugs are held in contact with the plaque, lesion or problematic tissue T on the wall of the vein V for a desired period of time to produce the desired effect. Drugs useful in treating plaques, lesions and problematic tissue are well known to those skilled in the art and include, paclitaxel and antimicrobial agents such as, for example, from triclosan from triclosan, chlorhexidine, nitrofurazone, benzalkonium chlorides, silver salts and antibiotics such as rifampin, gentamycin and minocyclin and combinations thereof, among others. In certain embodiments, antimicrobial agents may include triclosan, chlorhexidine and salts or combinations thereof. Anti-inflammatory agents include steroidal and non-steroidal anti-inflammatory agents. Examples of nonsteroidal anti-inflammatory drugs include aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid and its derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine a-acetic acid, salicylsulfuric acid, salsalate and sulfasalazine; thiazinecarboxamides such as droxicam, isoxicam, piroxicam and tenoxicam; others such as E-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Examples of steroidal anti-inflammatory agents (glucocorticoids) include 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Analgesic agents include narcotic and non-narcotic analgesics. Narcotic analgesic agents include alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof. Non-narcotic analgesics include aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide a-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Local anesthetic agents include amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Antispasmodic agents include alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-1 trimethyl-3,3-diphenyl-propylamine, tropenzile, trospium chloride, xenytropium bromide, and pharmaceutically acceptable salts thereof.

In certain embodiments, therapeutic agents for reducing pain or discomfort may be selected from ketorolac and pharmaceutically acceptable salts thereof (e.g., the tromethamine salt thereof, sold under the commercial name Torado®), 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial name Ditropang®), and combinations thereof. The amount of therapeutic agent present, will depend, for example, upon the efficacy of the therapeutic agent employed, the release rate, and so forth. One skilled in the art can readily determine an appropriate therapeutic agent loading to achieve the desired outcome.

While the ridges 78 and furrows 76 of the illustrated embodiment are in a regular, repeating pattern, it should be appreciated that the size and the location of each furrow 76 and each ridge 78 may be customized to match the vasculature of the patient and the position within that vasculature of the tissue to be ablated.

Figure 13:
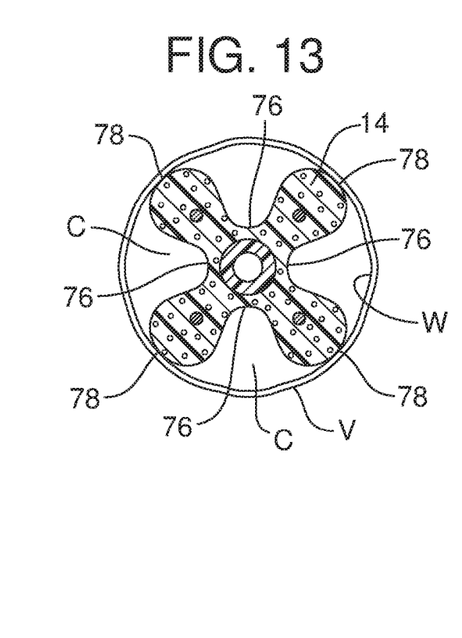
FIG. 13 is a cross sectional view of another alternative embodiment wherein the heat expandable element of muscle polymer has a corrugated profile in the transverse direction.

Reference is now made to FIG. 13 illustrating yet another embodiment of the medical device 10 including a heat expandable element 14, that when expanded in a vein V, has a corrugated profile or cross section in the transverse direction. In the illustrated embodiment, the heat expandable element 14 of muscle polymer includes four furrows 76 alternating with four ridges 78. The furrows 76 extend over the full length of the heat expandable element 14 from a first longitudinal end to a second longitudinal end.

When the heat expandable element 14 is fully expanded, each ridge 78 seals against the wall W of the vein V and each furrow 76 forms a flow channel C allowing blood to travel through the vein past the expanded heat expandable element 14.

Figure 14:
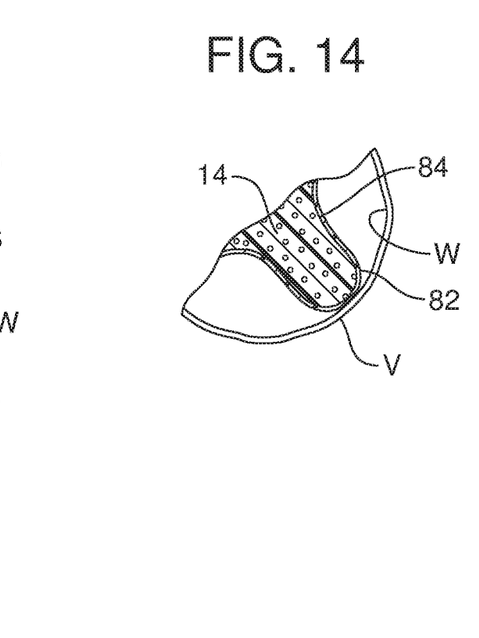
FIG. 14 is a detailed cross-sectional view illustrating an embodiment of the medical device including an insulating coating or membrane over an outer surface of the heat expandable element.

Reference is now made to FIG. 14 illustrating yet another possible embodiment of the medical device 10 including an insulating membrane 82 over an outer surface 84 of the muscle polymer of the heat expandable element 14. The insulating membrane 82 may be, for example, a silicone polymer coating. The insulating membrane 82 is adapted to provide some thermal insulating to the wall W of the vein V when the medical device 10 heats to a temperature above 44° C. during certain ablation procedures.

As briefly noted above, it should be appreciated that the medical device 10 may be customized to the vasculature of the patient thereby allowing for more efficient and effective treatment. Toward this end, a new method is provided for this purpose.

That method of customizing a medical device broadly incudes the steps of: making a 3D heat expandable element of muscle polymer that matches the vasculature of the patient and securing that heat expandable element to an elongated support or catheter 12. In other words, the heat expandable element 14 is made a specific size, length and shape to match the vasculature of the patient.

More specifically, the method may include the steps of scanning the anatomy or vasculature of the patient and generating a 3D image reconstruction of that vasculature. Scanning may include, but is not necessarily limited to, CT scans, MR scans, ultrasound scans and combinations thereof.

Next is the step of generating the heat expandable element 14 to match the vasculature of the patient. This can be done by creating a mold of the vasculature of the patient. More specifically, this may be achieved by 3D printing the vasculature as a phantom and making a mold of that phantom.

The method also includes the steps of: providing an elongated support or catheter 12 of desired length to match the vasculature of the patient and skiving the elongated support or catheter at specific points to expose the resistance heating wires 16 at selected locations along the length thereof. The elongated support or catheter 12 is then properly positioned within the mold and the heat expandable element 14 is cast in the mold around the elongated support or catheter. The finished medical device 10 is then removed from the mold.

In an alternative method, no mold is made. Instead, the heat expandable element 14 is 3D printed directly onto the skived catheter 12 of desired length based upon 3D modeling of the vasculature of the patient.

The disclosure may be considered to relate to the following items:
1. A medical device for ablating tissue, comprising:
   an elongated support; and
   a heat expandable element carried on the elongated support.
2. The medical device of item 1, wherein the heat expandable element is a body made from a muscle polymer.
3. The medical device of items 1 or 2, further including a heating element associated with the heat expandable element wherein when the heating element is activated, the heat expandable element is heated and expands to displace the heating element from a rest position to an expanded position in closer proximity to the tissue to be ablated.
4. The medical device of items 2 or 3, wherein the muscle polymer comprises an elastomeric polymer including micro-bubbles of liquid-gas phase change material.

5. The medical device of item 4, wherein the liquid-gas phase change material has a phase change temperature of between 40-100° C.
6. The medical device of items 4 or 5, wherein the elastomeric polymer is selected from a group of elastomeric polymers consisting of silicone, thermoplastic elastomer, styrenic and combinations thereof.
7. The medical device of any of items 4-6, wherein the liquid-gas phase change material is selected from a group of liquid-gas phase change materials consisting of ethanol, butanol and combinations thereof.
8. The medical device of any of items 2-7, wherein the muscle polymer is silicone ethanol.
9. The medical device of any of items 1-8, wherein the elongated support is a lumenless shaft.
10. The medical device of any of items 1-8, wherein the elongated support is a catheter including at least one lumen.
11. The medical device of any of items 1-10, wherein the elongated support includes a proximal end and a distal end.
12. The medical device of item 11, wherein the proximal end includes a handle.
13. The medical device of item 12, wherein the handle includes an actuator switch to control the operation of the heating element.
14. The medical device of item 13, wherein the actuator is selected from a group consisting of a push button, a toggle switch, a slide switch and a twist knob.
15. The medical device of any of claims 12-14, wherein the handle houses a power source.
16. The medical device of any of items 12-15, wherein the handle includes a power cord configured for connection to a remote power source.
17. The medical device of any of items 12-16, wherein the handle includes a drug delivery port.
18. The medical device of any of items 1-17, wherein the heating element is a resistive wire embedded in the heat expandable element.
19. The medical device of item 18, wherein the resistive wire extends through the elongated support to the heat expandable element.
20. The medical device of item 19, wherein the resistive wire includes an array of resistive wires extending around a circumference of the elongated support in the heat expandable element.
21. The medical device of any of items 2-20, wherein the body is a sleeve 3-D printed onto the elongated support.
22. The medical device of any of items 2-20, wherein the body is a sleeve molded onto the elongated support.
23. The medical device of any of items 2-20, wherein the body extends 360° around the elongated support.
24. The medical device of any of items 1-23, further including a wire connecting cap at the distal end of the catheter.
25. The medical device of any of items 2-24, further including a scoring element carried on the muscle polymer.
26. The medical device of item 25, wherein the scoring element is at least one wire.
27. The medical device of any of items 2-26, wherein the muscle polymer has a corrugated profile in a transverse direction.
28. The medical device of any of items 2-26, wherein the muscle polymer has a corrugated profile in a longitudinal direction.
29. The medical device of any of items 2-28, wherein the muscle polymer includes at least one flow channel extending from a first longitudinal end of the muscle polymer to a second longitudinal end of the muscle polymer.
30. The medical device of any of items 2-29, further including an insulating membrane over an outer surface of the muscle polymer.
31. The medical device of item 30, wherein the insulating membrane is a silicone polymer coating.
32. A method of ablating tissue of a varicose vein, comprising:
    positioning an elongated support in the varicose vein;
    activating a heating element associated with a heat expandable element carried on the elongated support; and
    expanding the heat expandable element in response to heat from the heating element and thereby displacing the heating element into closer proximity to the tissue to be ablated.
33. The method of item 32, further including (a) deactivating the heating element and (b) retracting the heat expandable element in response to cooling of the heating element.
34. The method of item 33, including repositioning the elongated support in the varicose vein.
35. The method of item 34, including (a) reactivating the heating element and (b) re-expanding the heat expandable element in response to the heat from the reactivated heating element and thereby displacing the heating element into closer proximity to additional tissue to be ablated.
36. The method of items 32-35, including using a body made from a muscle polymer as the heat expanding element.
37. The method of item 36 wherein activating the heating element includes directing a current through a resistive wire embedded in the heat expandable element.
38. The method of any of items 32-37, including expanding the heat expandable element to an expanded position by heating micro-bubbles of a liquid-gas phase change material embedded in an elastomeric polymer of the heat expandable element to a temperature sufficient to cause a phase change from liquid to gas.
39. The method of any of items 32-38, including retracting the heat expandable element to a rest position by cooling micro-bubbles of a liquid-gas phase change material embedded in an elastomeric polymer of the heat expandable element to a temperature sufficient to cause a phase change from gas to liquid.
40. A method of customizing a medical device to vasculature of a specific patient undergoing treatment, comprising:
    making a 3D heat expandable element of muscle polymer that matches the vasculature of the specific patent; and
    securing the 3D expandable element to an elongated support.
41. The method of item 40, including scanning the vasculature of the specific patient and generating a 3D image reconstruction of the vasculature.
42. The method of item 41, further including completing a CT scan, an MR scan, an ultrasound scan and combinations thereof.
43. The method of items 40-42, further including generating the heat expandable element to match the vasculature of the specific patient.

44. The method of item 43, wherein the generating of the heat expandable element is accomplished by creating a mold of the vasculature of the specific patient.
45. The method of item 44, including 3D printing the vasculature as a phantom and making a mold of the phantom.
46. The method of items 40-45, further including (a) providing an elongated support of length to match the vasculature and (b) skiving the elongated support at specific points to expose at least one resistance heating wire at selected locations along a length of the elongated support.
47. The method of item 46, including positioning the elongated support within the mold and casting the heat expandable element in the mold around the elongated support.
48. The method of item 47, including removing the medical device from the mold.
49. The method of items 40-43, including (a) providing an elongated support of length to match the vasculature and (b) skiving the elongated support at specific points to expose at least one resistance heating wire at selected locations along a length of the elongated support.
50. The method of item 49, including 3D printing the heat expandable element directly onto the skived elongated body.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of". Each of the phrases "consisting of and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms parallel or perpendicular are meant to mean approximately meeting this condition, unless otherwise specified.

It is to be fully understood that certain aspects, characteristics, and features, of the medical device and method, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the medical device and method which are illustratively described and presented in combination or sub-combination in the context or format of a single embodiment may also be illustratively described and presented in the context or format of a plurality of separate embodiments.

Although the medical device and method of this disclosure have been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

The foregoing has been presented for purposes of illustration and description. It is not intended to be exhaustive or to limit the embodiments to the precise form disclosed. Obvious modifications and variations are possible in light of the above teachings. For example, a strain relief of a type known in the art may be provided between the elongated body 12 and the handle 30. The strain relief may be an extrusion of various types of plastic such as PEBAX® brand PEBA, Nylon, PET, etc. It should be appreciated that the medical device 10 may include an external sleeve over the heat expandable element 14 to protect the heat expandable element as it tracts to the treatment zone. That sleeve could be similar to sleeves used in stent deployment devices. All such modifications and variations are within the scope of the appended claims when interpreted in accordance with the breadth to which they are fairly, legally and equitably entitled.

What is claimed:
1. A medical device for ablating tissue in connection with a power source, comprising:
    an elongated support;
    a heat expandable element secured to the elongated support; and
    a heating element adapted for heating the heat expandable element via the power source so as to cause said heat expandable element to expand from a rest position to an expanded position in closer proximity to the tissue to be ablated;
    wherein the heat expandable element comprises a body made from a muscle polymer.

2. The medical device of claim 1, wherein the muscle polymer comprises an elastomeric polymer including micro-bubbles of liquid-gas phase change material.

3. The medical device of claim 2, wherein the liquid-gas phase change material has a phase change temperature of between 40-100° C.

4. The medical device of claim 2, wherein the elastomeric polymer is selected from a group of elastomeric polymers consisting of silicone, thermoplastic elastomer, styrenic and combinations thereof.

5. The medical device of claim 2, wherein the liquid-gas phase change material is selected from a group of liquid-gas phase change materials consisting of ethanol, butanol and combinations thereof.

6. The medical device of claim 1, wherein the muscle polymer is silicone ethanol.

7. The medical device of claim 1, wherein the elongated support is a lumenless shaft.

8. The medical device of claim 1, wherein the elongated support is a catheter including at least one lumen.

9. The medical device of claim 1, wherein the elongated support includes a proximal end and a distal end.

10. The medical device of claim 9, wherein the proximal end includes a handle.

11. The medical device of claim 10, further including an actuator to control the operation of the heating element, the actuator being attached to the handle.

12. The medical device of claim 11, wherein the actuator is selected from a group consisting of a push button, a toggle switch, a slide switch and a twist knob.

13. The medical device of claim 10, wherein the handle houses the power source.

14. The medical device of claim 10, wherein the handle is connected to a power cord configured for connection to a remote power source.

15. The medical device of claim 10, wherein the handle includes a drug delivery port.

16. The medical device of claim 1, wherein the heating element is a resistive wire embedded in the heat expandable element.

17. The medical device of claim 16, wherein the resistive wire extends through the elongated support to the heat expandable element.

18. The medical device of claim 17, wherein the resistive wire includes an array of resistive wires extending around a circumference of the elongated support in the heat expandable element.

19. The medical device of claim 1, wherein the body is a sleeve 3-D printed onto the elongated support.

20. The medical device of claim 1, wherein the body is a sleeve molded onto the elongated support.

21. The medical device of claim 1, wherein the body extends around the elongated support.

22. The medical device of claim 1, further including a wire connecting cap at the distal end of the elongated support.

23. The medical device of claim 1, further including a scoring element carried on the muscle polymer.

24. The medical device of claim 23, wherein the scoring element is at least one wire.

25. The medical device of claim 1, wherein the muscle polymer has a corrugated profile in a transverse direction.

26. The medical device of claim 1, wherein the muscle polymer has a corrugated profile in a longitudinal direction.

27. The medical device of claim 1, wherein the muscle polymer includes at least one flow channel extending from a first longitudinal end of the muscle polymer to a second longitudinal end of the muscle polymer.

28. The medical device of claim 1, further including an insulating membrane over an outer surface of the muscle polymer.

29. The medical device of claim 28, wherein the insulating membrane is a silicone polymer coating.

30. A medical device for ablating tissue in connection with a power source, comprising:
   an elongated support;
   a heat expandable element secured to the elongated support; and
   a heating element adapted for heating the heat expandable element via the power source so as to cause said heat expandable element to expand from a rest position to an expanded position in closer proximity to the tissue to be ablated;
   wherein the heat expandable element comprises an elastomeric polymer including micro-bubbles of liquid-gas phase change material.

31. A medical device for ablating tissue in connection with a power source, comprising:
   an elongated support;
   a heat expandable element secured to the elongated support;
   a heating element adapted for heating the heat expandable element via the power source so as to cause said heat expandable element to expand from a rest position to an expanded position in closer proximity to the tissue to be ablated;
   wherein the elongated support includes a proximal end and a distal end;
   wherein the proximal end includes a handle; and
   further including an actuator to control the operation of the heating element, the actuator being attached to the handle.

32. A medical device for ablating tissue in connection with a power source, comprising:
   an elongated support;
   a heat expandable element secured to the elongated support; and
   a heating element adapted for heating the heat expandable element via the power source so as to cause said heat expandable element to expand from a rest position to an expanded position in closer proximity to the tissue to be ablated;
   wherein the heating element is a resistive wire embedded in the heat expandable element.

33. The medical device of claim 32, wherein the resistive wire extends through the elongated support to the heat expandable element.

34. The medical device of claim 32, wherein the resistive wire includes an array of resistive wires extending around a circumference of the elongated support in the heat expandable element.

* * * * *